(12) United States Patent
Siochi

(10) Patent No.: US 6,757,355 B1
(45) Date of Patent: *Jun. 29, 2004

(54) HIGH DEFINITION RADIATION TREATMENT WITH AN INTENSITY MODULATING MULTI-LEAF COLLIMATOR

(75) Inventor: Ramon Alfredo Carvalho Siochi, Apex, NC (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 280 days.

This patent is subject to a terminal disclaimer.

(21) Appl. No.: 09/642,553

(22) Filed: Aug. 17, 2000

(51) Int. Cl.$^7$ .................................................. A61N 5/10
(52) U.S. Cl. .......................... 378/65; 378/64; 378/147; 378/152; 378/153
(58) Field of Search .......................... 378/64, 65, 147, 378/152, 153

(56) References Cited

U.S. PATENT DOCUMENTS

| | | | | |
|---|---|---|---|---|
| 5,216,255 A | | 6/1993 | Weidlich | 250/492.3 |
| 5,332,908 A | * | 7/1994 | Weidlich | 250/492.1 |
| 5,651,043 A | * | 7/1997 | Tsuyuki et al. | 378/65 |
| 5,663,999 A | | 9/1997 | Siochi | 378/65 |
| 5,724,403 A | | 3/1998 | Siochi et al. | 378/150 |
| 5,740,225 A | * | 4/1998 | Nabatame | 378/65 |
| 5,748,703 A | * | 5/1998 | Cosman | 378/152 |
| 5,818,902 A | | 10/1998 | Yu | 378/65 |
| 6,052,430 A | * | 4/2000 | Siochi et al. | 378/65 |
| 6,128,366 A | * | 10/2000 | Siochi | 378/65 |
| 6,134,296 A | * | 10/2000 | Siochi | 378/65 |
| 6,240,161 B1 | * | 5/2001 | Siochi | 378/65 |
| 6,260,999 B1 | * | 7/2001 | Wofford et al. | 378/205 |
| 6,266,393 B1 | * | 7/2001 | Ein-Gal | 378/152 |
| 6,314,159 B1 | * | 11/2001 | Siochi | 378/65 |
| 6,322,249 B1 | * | 11/2001 | Wofford et al. | 378/207 |
| 6,330,300 B1 | * | 12/2001 | Siochi | 378/65 |
| 6,335,961 B1 | * | 1/2002 | Wofford et al. | 378/65 |

FOREIGN PATENT DOCUMENTS

| | | |
|---|---|---|
| GB | 2342552 A | 4/2000 |
| GB | 2346057 A | 7/2000 |
| GB | 22361399 A | 10/2001 |
| JP | 7255718 A | 9/1995 |

* cited by examiner

Primary Examiner—Drew A. Dunn
Assistant Examiner—Allen C. Ho

(57) ABSTRACT

A method for delivering radiation from a radiation source to treatment a area utilizing a multi-leaf collimator. The method includes positioning the multi-leaf collimator between the radiation source and the object to block a portion of the radiation. The leaves of the multi-leaf collimator are generally located within a plane and extend longitudinally along a first axis. The leaves are positioned to define a first treatment field. The method further includes delivering radiation to the first treatment field and rotating the multi-leaf collimator about a central axis extending generally perpendicular to the leaf plane. The leaves are positioned to define a second treatment field and radiation is delivered to the second treatment field

18 Claims, 11 Drawing Sheets

HIGH DEFINITION RADIATION TREATMENT WITH AN INTENSITY MODULATING MULTI-LEAF COLLIMATOR

FIELD OF THE INVENTION

The present invention relates generally to a radiation emitting device, and more particularly, to a method for delivering radiation treatment.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

Methods for making the treatment volume correspond more closely with a tumor include defining the tumor shape with a lead alloy block, moving solid jaw blocks during treatment, scanning the radiation beam over the volume to be treated, and using a multi-leaf collimator to create an irregularly shaped field corresponding generally to the shape of the tumor. The multi-leaf collimator includes two opposing arrays of side-by-side elongated radiation blocking collimator leaves. Each leaf can be moved longitudinally towards or away from the central axis of the beam, thus defining a desired shape through which the radiation beam will pass. Multi-leaf collimators are increasingly being used to replace lead alloy blocks in many conformal radiation treatments to reduce costs and time required to create the block. However, there are still a number of treatment cases that require the use of blocks since conformal shaping can not be adequately accomplished using a multi-leaf collimator. This is due to a "stair-step" effect that occurs along field edges that are not perpendicular to leaf face edges. An undulating dose pattern at the border of an irradiated volume results when the leaves are stepped to create an irregular shape. This distribution is unacceptable for field edges that are adjacent to critical structures or when abutment of additional fields is planned.

One method for reducing this stair-step effect is to divide the treatment dose into multiple intensity fields and shift the table supporting the patient between deliveries of each intensity field. However, this is often undesirable since the table shifts move the planned isocenter.

Another possible solution is to provide a collimator with thinner leaves. However, the hardware required for the additional leaves is expensive, adds weight to the system, may reduce clearance between the treatment head and the patient, and may decrease reliability and life of the system.

Accordingly, there is therefore, a need for a method for achieving higher spatial resolution intensity modulation to reduce stair-step effects at critical borders during radiation therapy without changing current multi-leaf collimator leaf widths or shifting the patient during radiation treatment.

SUMMARY OF THE INVENTION

A method for delivering radiation from a radiation source to a treatment area utilizing a multi-leaf collimator is disclosed. The method includes positioning the multi-leaf collimator between the radiation source and the treatment area to block a portion of the radiation. The leaves of the multi-leaf collimator extend longitudinally along a first axis and are positioned to define a first treatment field. The method further includes delivering radiation to the first treatment field and rotating the multi-leaf collimator about a central axis extending generally perpendicular to the leaf plane. The leaves are positioned to define a second treatment field and radiation is delivered to the second treatment field.

In one embodiment, the collimator is rotated until the leaves extend longitudinally along a second axis generally perpendicular to the first axis. The leaves may be moved longitudinally to create additional treatment fields. A prescribed radiation dose is preferably divided equally among the different treatment fields.

The method may further include dividing the treatment area into a plurality of cells, each having a defined treatment intensity level. The cells are grouped to form a plurality of matrices, each of the matrices having at least one dimension approximately equal to a width of the collimator leaf. Each of the matrices is decomposed into orthogonal matrices for delivery with a zero degree offset collimator and a ninety degree offset collimator.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention and is provided in the context of a patent application and its requirements. Various modifications to the preferred embodiments will be readily apparent to those skilled in the art and the generic principles herein may be applied to other embodiments. Thus, the present invention is not intended to be limited to the embodiment shown but is to be accorded the widest scope consistent with the principles and features described herein.

Figure 1:
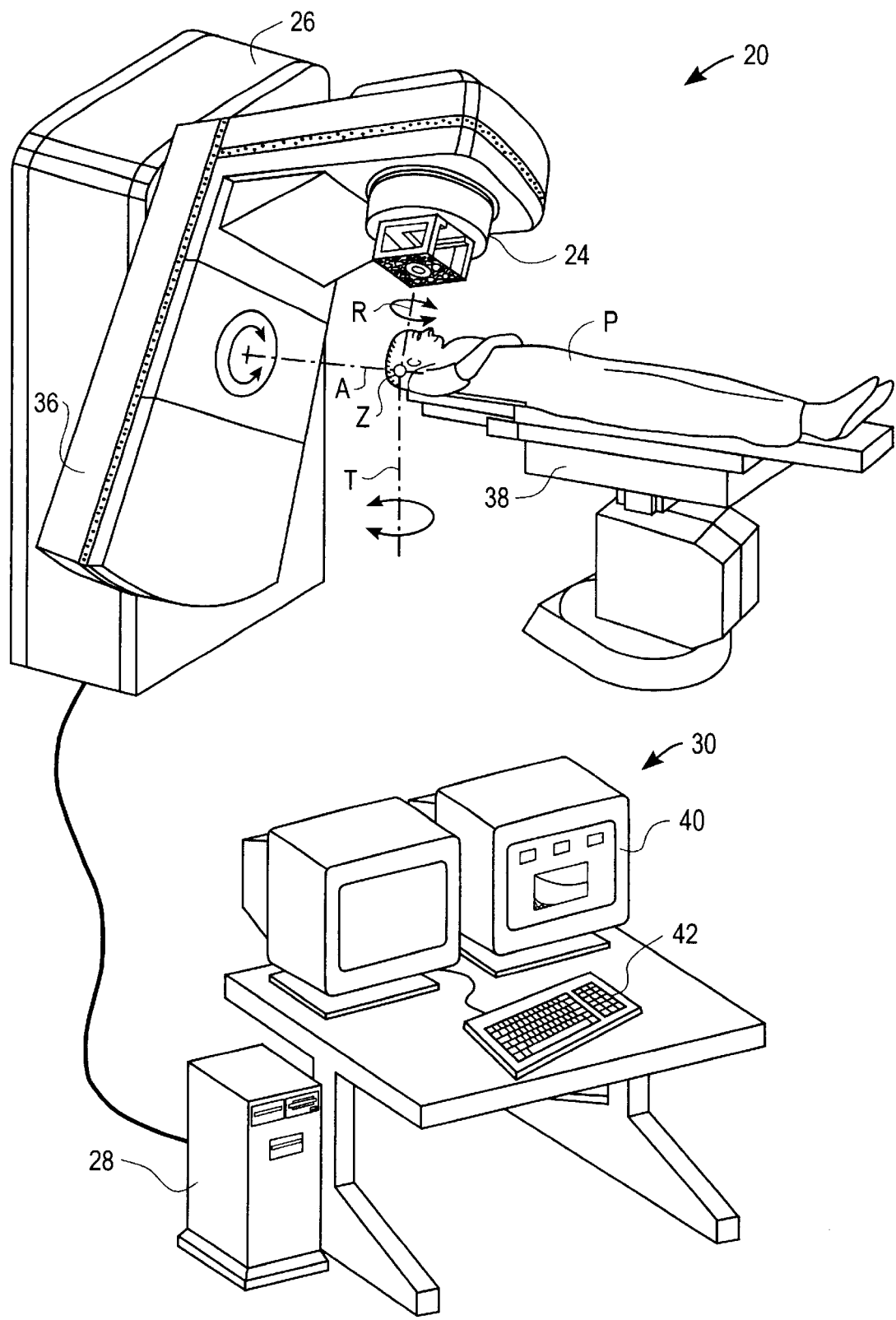
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The rotable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
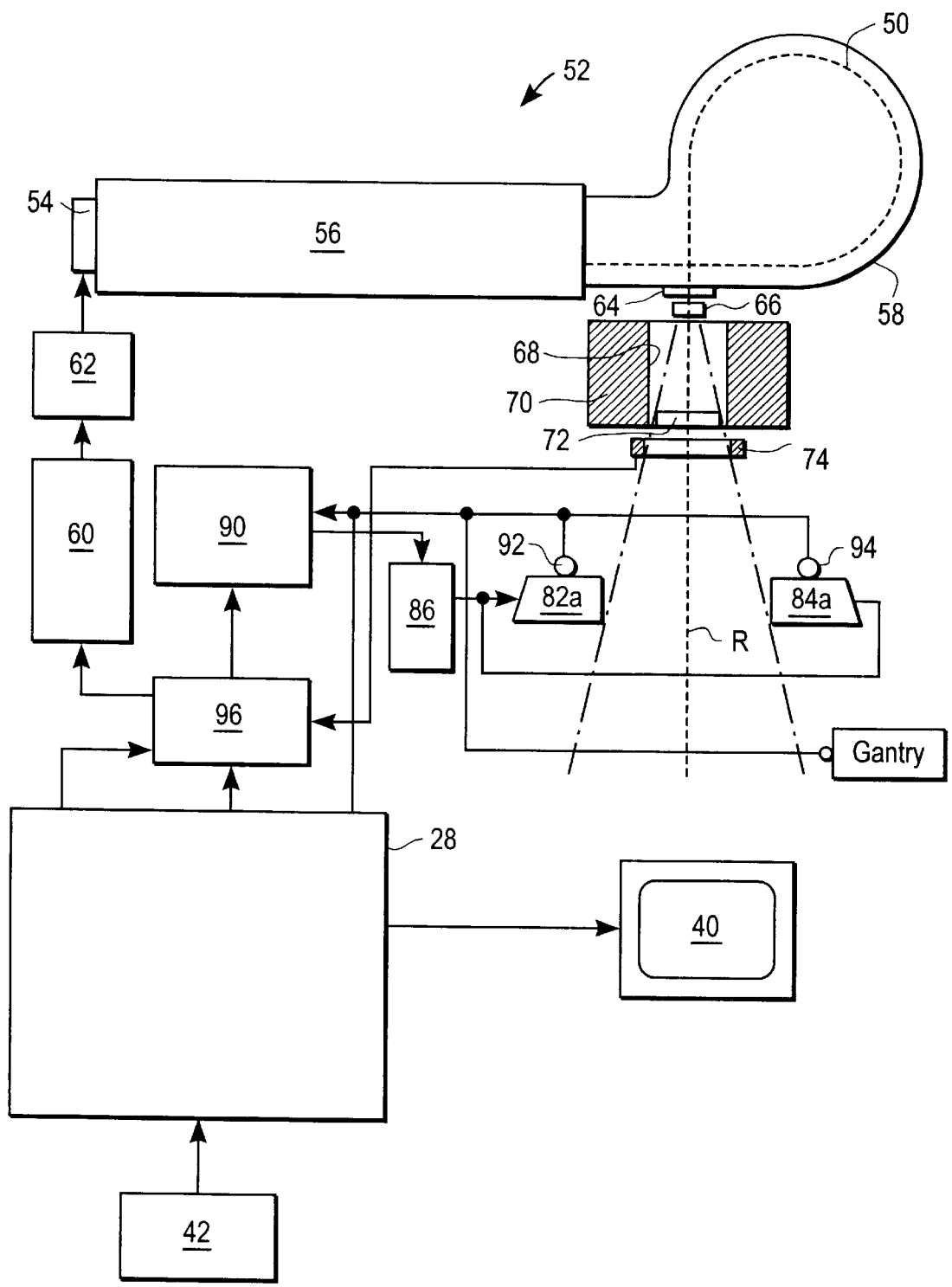
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
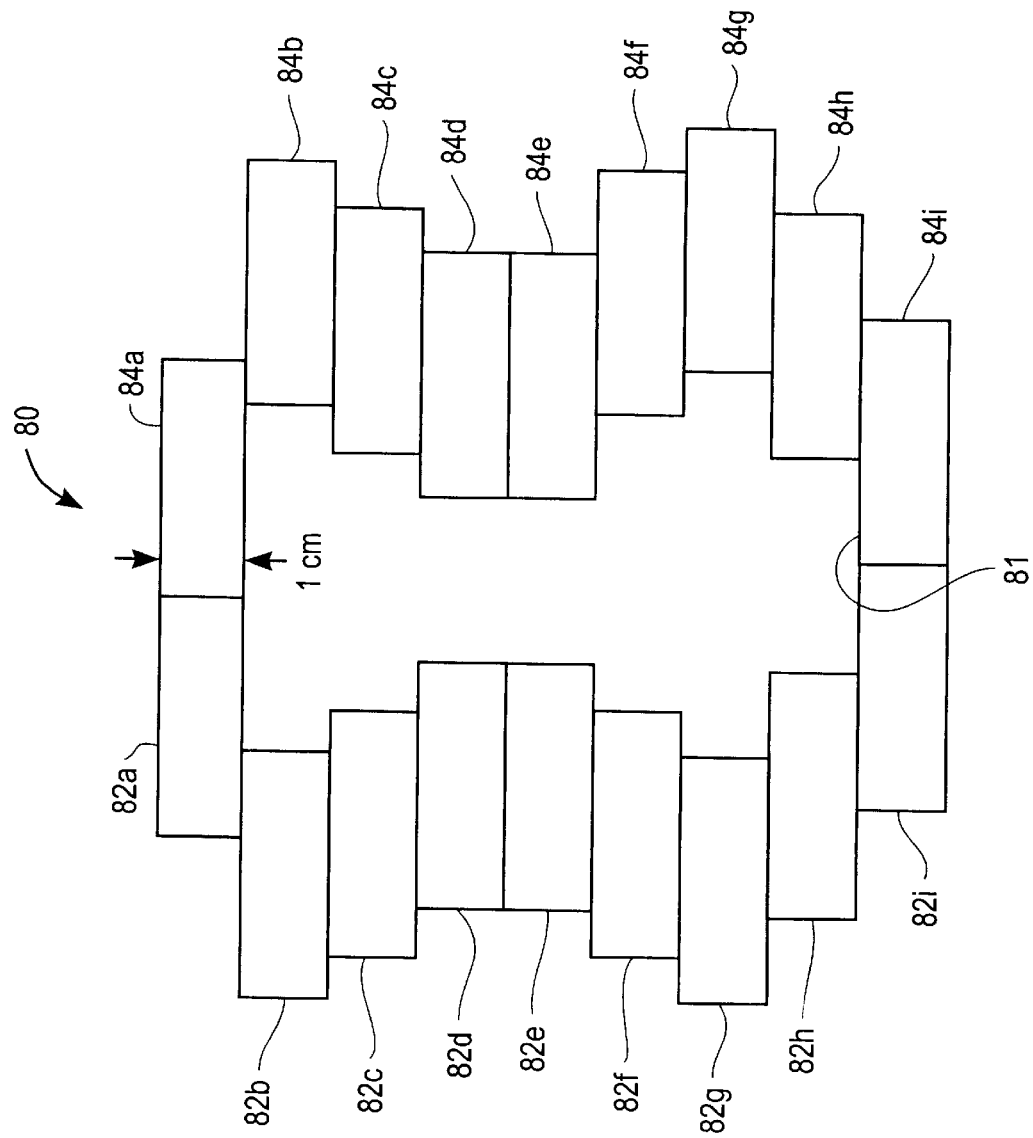
FIG. 3 is a plan view illustrating leaves of a multi-leaf collimator positioned for treatment in the radiation treatment device of FIG. 1.

A beam shielding device, generally indicated at 80, is provided in the path of the beam 50 to define a radiation field 81 (FIGS. 2 and 3). The beam shielding device 80 includes a plurality of opposing plates or leaves 82a–i and 84a–i, only two of which are shown in FIG. 2 for simplification. FIG. 3 illustrates leaves 82a–i and 84a–i (forming leaf pairs 82a and 84a, 82b and 84b, . . . 82i and 84i) of a multi-leaf collimator mounted between the radiation source and patient and positioned to define a treatment field by delimiting the electron beam 50. The leaves 82a–i, 84a–i typically have a one centimeter width and are substantially impervious to the emitted radiation so that they block healthy tissue from the radiation.

The leaves 82a–i, 84a–i are movable in a direction generally perpendicular to axis R by a drive unit 86 (which is shown in FIG. 2 only with respect to plate 82a) to change the size of the irradiated field so that the distribution of radiation over the field does not need to be uniform (i.e., one region may be exposed to a higher dose than another region). The drive unit 86 includes an electric motor which is coupled to the plate 82a and controlled by a motor controller 90. Position sensors 92, 94 are also coupled to plates 82a, 84a, respectively, for sensing their positions. The drive unit 86 drives the plate 82a in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82a, 84a. The central processing unit 28 controls execution of the program and the opening and closing of the collimator plates 82a, 84a to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention. The treatment device 20 described above is provided merely as an example of a device for use in delivering a treatment according to the method described below.

The following describes methods of the present invention for delivering radiation to a treatment area with a multi-leaf collimator operable to rotate about axis R of the radiation beam, which coincides with a central axis extending generally perpendicular to a plane containing at least a portion of the leaves of the multi-leaf collimator (FIG. 1). The methods involve applying a first radiation treatment to a treatment area with the collimator in a first position and then rotating the collimator about axis R and applying a second radiation treatment. In order to reduce the stair-step effect created by the width of the leaves, the radiation is delivered in two or more separate treatment fields, the first one with the collimator in a zero degree offset orientation and the second one with the collimator offset approximately ninety degrees from the first collimator position. The zero degree offset orientation of the collimator may be selected according to procedures used to select the optimum collimator orientation for conventional multi-leaf collimator radiation delivery (i.e., no collimator rotation about axis R). Software products such as Beamshaper may be used to determine the optimum collimator orientation, as is well known by those skilled in the art. As described below, the collimator is preferably rotated approximately ninety degrees relative to the zero degree position, however, the two collimator positions may be spaced at an angular rotation other than ninety degrees, or the radiation may be applied with the collimator positioned in more than two angular orientations, without departing from the scope of the invention.

The first method described below involves positioning the leaves so that a leading edge of each leaf intersects a border of the treatment area at the specified location. The second method involves defining an intensity map on the treatment area and positioning the leaves based on the intensity map. The second method is preferred if the border of the treatment area has steep (large slope) sections, short sections, or sharp changes in curvature.

Figure 4:
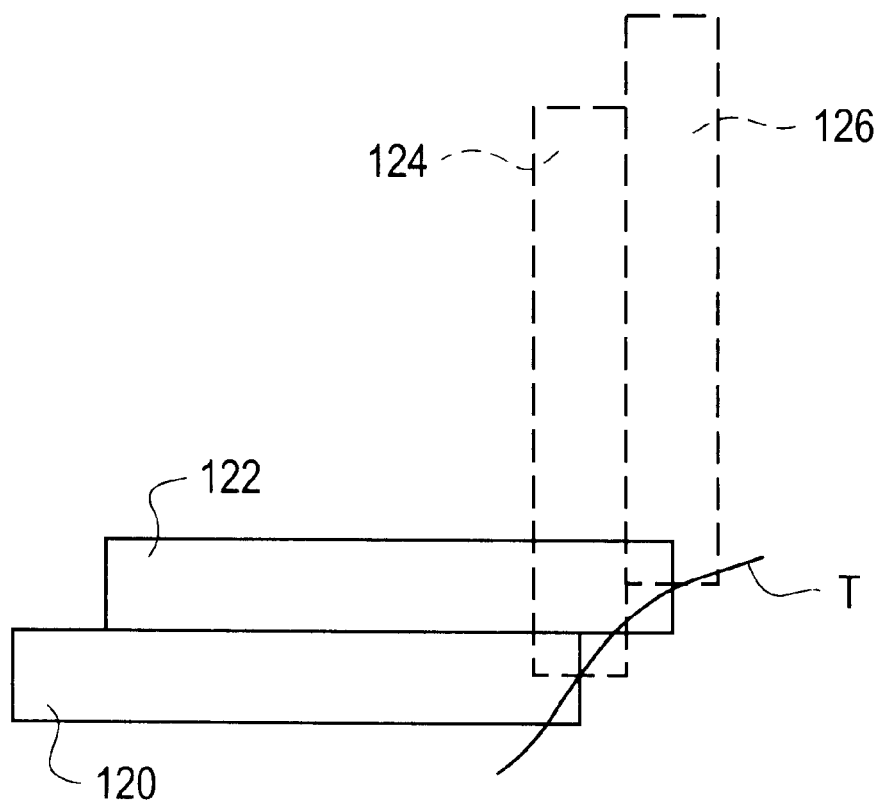
FIG. 4 is a plan view illustrating a portion of the leaves of the multi-leaf collimator positioned in a first position and leaves shown in phantom with the collimator positioned in a second position.
Figure 4:
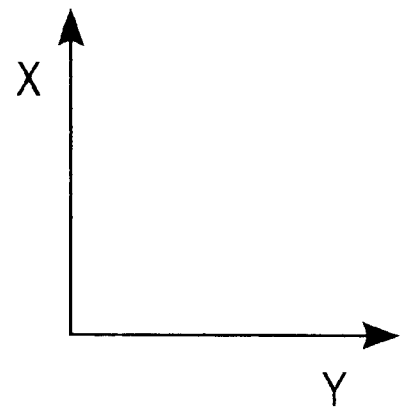
Figure 5:
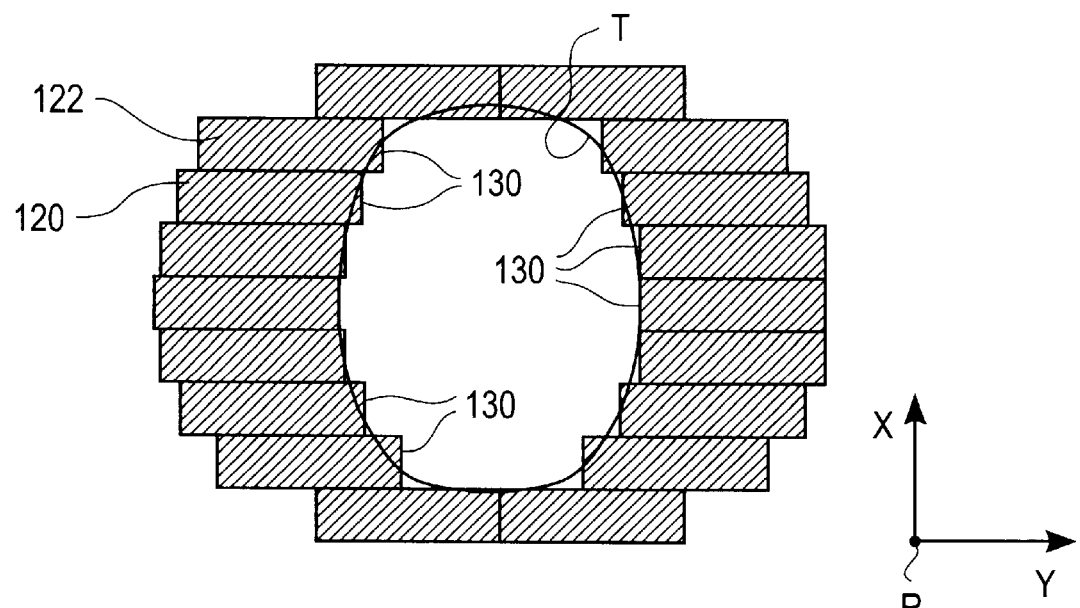
FIG. 5 is a plan view of the multi-leaf collimator positioned in a zero degree offset position.
Figure 6:
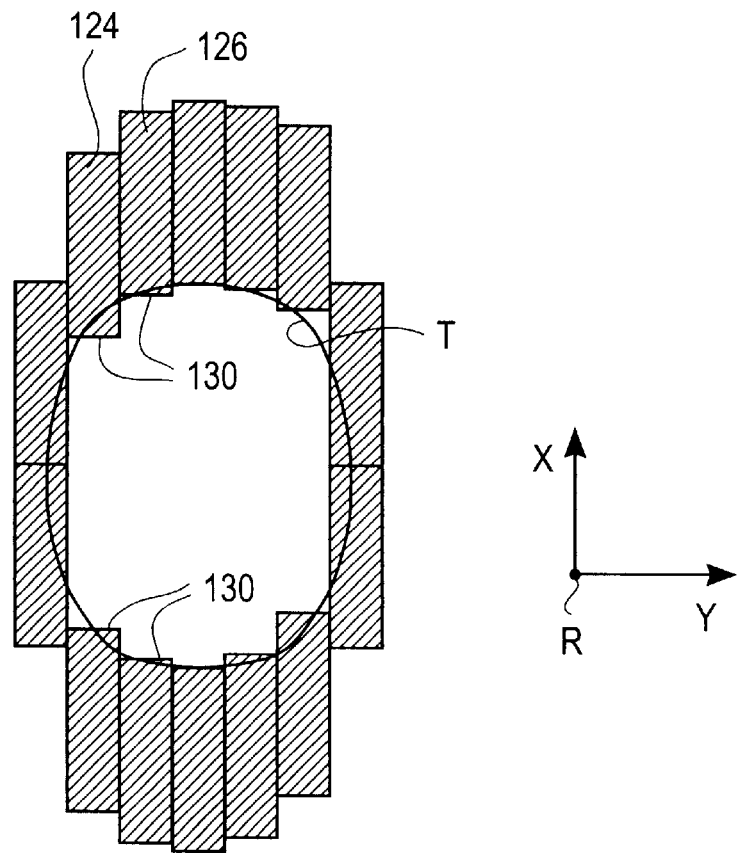
FIG. 6 is a plan view of the multi-leaf collimator of FIG. 5 positioned in a ninety degree offset position.
Figure 7:
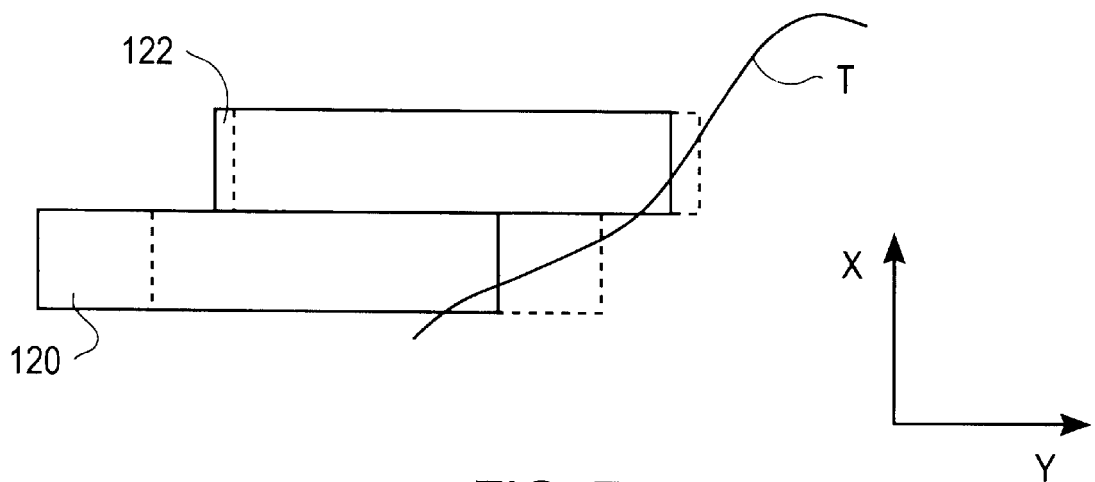
FIG. 7 is a plan view of two leaves intersecting a border of a treatment area, with the leaves shown in a second position in phantom.
Figure 8:
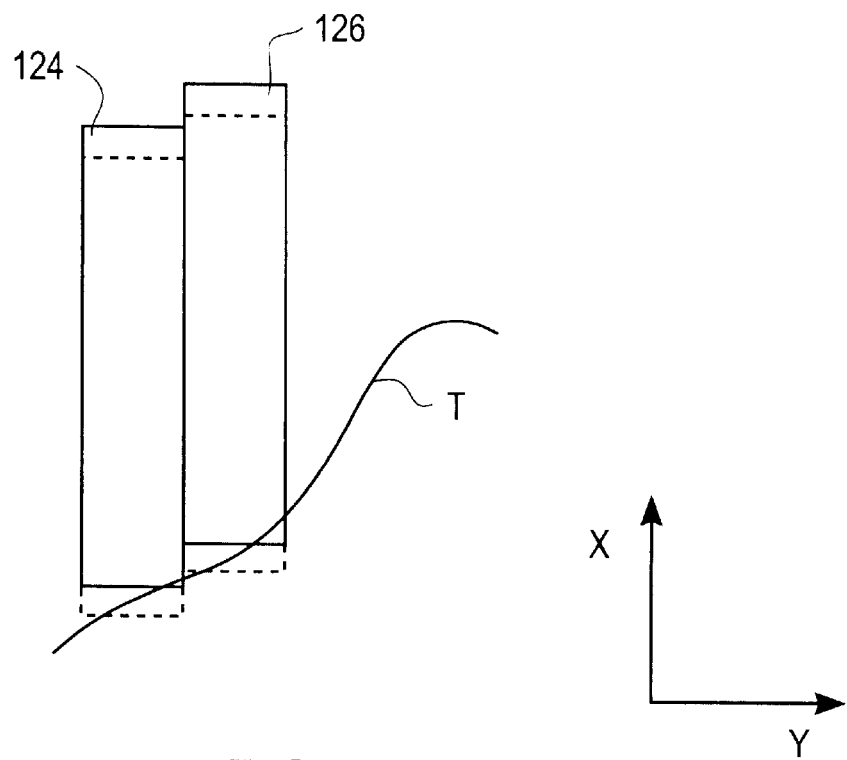
FIG. 8 is a plan view of two leaves intersecting the border of the treatment area, with the collimator rotated from its zero degree offset position and the leaves shown in a second position in phantom.

FIG. 4 shows a partial plan view of a treatment area T and a portion of the leaves of the multi-leaf collimator positioned in two different orientations to define a border of the treatment area. Leaves 120 and 122 extend longitudinally along a y-axis with the collimator positioned in its zero degree offset orientation (FIGS. 4 and 5). Leaves 124 and 126 (shown in phantom in FIG. 4) extend longitudinally along an x-axis when the collimator is positioned in its ninety degree offset position (FIGS. 4 and 6). FIG. 4 illustrates that the resolution at the border of the target area can be increased by applying the radiation in two different collimator orientations. The leaves may also be moved longitudinally while the collimator remains in its same orientation to further increase the resolution. As shown in FIGS. 7 and 8, leaves 120, 122 and 124, 126 intersect a periphery edge (border) of the treatment area T with the collimator positioned in its zero degree offset orientation and ninety degree offset orientation, respectively. The leaves are shown in phantom offset longitudinally from a first position to create a new treatment field. The number of leaf positions and collimator orientations required to reduce the stair-step effect depends on how fine or "smooth" a contour is desired. Any number of intensity fields may be used to deliver the radiation at different collimator orientations and various longitudinal leaf positions to provide the desired contour along the periphery edge of the treatment area T.

In the first method for defining leaf positions for the different treatment fields, the position of each leaf relative to the periphery edge of the treatment area T is based on the number of treatments fields to be delivered. If only two treatment fields are delivered each leaf will be positioned such that the transverse edge (i.e., leading face) 130 of each leaf intersects the border of the treatment area at approximately its midpoint (i.e., one half of the leaf width) (FIGS.

5 and 6). Thus, the collimator will first be positioned at its zero degree offset orientation with each leaf positioned to intersect the treatment area border at its midpoint as shown in FIG. 5. Half of the radiation dose is delivered with the leaves defining this first treatment field. The collimator is then rotated about central axis R until the leaves extend generally orthogonal to their original leaf position (FIG. 6). The leaves are each moved longitudinally along the x-axis until each leaf intersects the border at approximately the midpoint of the leaf edge 130. The remaining half of the radiation dosage is delivered with the leaves positioned to define this second treatment field.

If three separate treatment fields are used, one field may be delivered with the multi-leaf collimator in a first orientation and the other two fields delivered with the multi-leaf collimator in a second orientation. For example, the first treatment field may be delivered as described above and shown in FIG. 5 for the two treatment field case. The collimator is then rotated to its second orientation (e.g., rotated ninety degrees from the first collimator orientation) and radiation is delivered over two separate treatment fields with the leaves intersecting two different points along the border, as shown in FIG. 8 and described below.

If four different treatment fields are used, the prescribed number of monitor units of radiation is divided into four equal doses, with one quarter of the radiation being delivered for each treatment field. FIGS. 7 and 8 show leaves positioned for two treatment fields with the collimator in its zero degree offset position and two treatment fields with the collimator in its ninety degree offset position, respectively. Radiation is first delivered with the leaves 120, 122 positioned to intersect the treatment area border at a location approximately one-third of the way along the transverse edge 130 of each leaf (FIG. 7). The leaves 120, 122 are then moved longitudinally (as shown in phantom) until each leaf intersects the border at a location approximately two-thirds of the way along the transverse edge of the leaf.

The following equation may be used to determine the number of leaf positions required for each collimator orientation with a given number of treatment fields:

$$m = n/2 \text{ (for even number of fields);}$$

where:
n=number of treatment fields; and
m=number of leaf positions for each collimator orientation.

The amount of prescribed monitor units of radiation delivered for each field will be 1/n. The intersection of the leaves and border for each position will be at intervals of 1/(m+1) times the leaf width. For example, if a 1 cm width leaf is used and the radiation is to be delivered over six treatment fields the number of leaf positions for each collimator orientation (e.g., zero degree offset and ninety degree offset) will be:

$$m = 6/2 = 3;$$

and the intersection between each leaf and border will be at intervals of:

$$1/(3+1) = \tfrac{1}{4} \times 1 \text{ cm.}$$

Thus, the intersection points are at ¼ cm, ½ cm, and ¾ cm of the total leaf width along the transverse edge 130 of the leaf.

If the number of intensity fields is odd (i.e., n=2m+1), the points along the leaf will be at intervals of 1/(m+1) times the leaf width in one collimator orientation and 1/(m+2) in the other collimator orientation. The collimator orientation for which the larger number of fields are delivered is preferably the ninety degree offset orientation if the zero degree offset orientation has a collimator angle that has already been optimized to minimize the stair-step effect. In the case where the zero degree offset position has not been selected through an optimization process, the collimator orientation that can be best fit with a single treatment field application is preferably selected as the orientation that receives fewer radiation applications.

Figure 9:
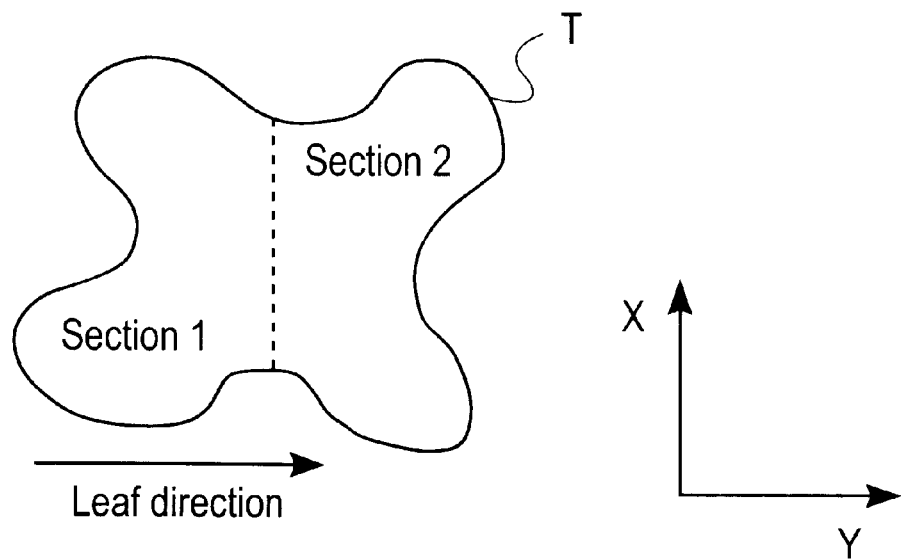
FIG. 9 is a plan view of a treatment area divided into two sections for radiation delivery with the collimator positioned in its zero degree offset orientation.
Figure 10:
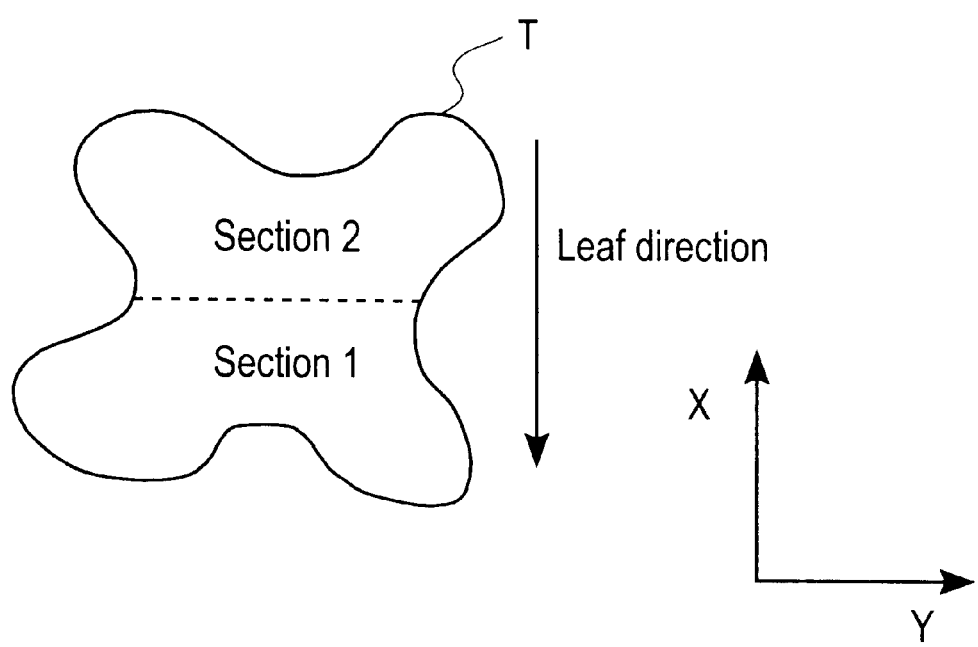
FIG. 10 is a plan view of the treatment area of FIG. 9 divided into two sections for radiation delivery with the collimator positioned in its ninety degree offset orientation.

If a treatment area T has concave and convex regions, it is difficult to position the leaves such that each leaf has a unique intersection point along the border of the treatment area. The treatment area T may be divided into two or more separate regions, as indicated by the dashed lines shown on the treatment areas of FIGS. 9 and 10. Each section of the treatment area now has a unique set of intersection points and each section receives the same number of monitor units of radiation prescribed for the treatment area. The treatment fields are generated individually for each section of the treatment area T, as previously described. Since the dividing line is based on the collimator orientation, the treatment area T is divided differently for each orientation. The leaves used to define the dividing line are preferably offset slightly from the line to leave a margin adjacent to the line. This is used to correct for under dosages that can occur at the dividing line. As indicated in FIGS. 9 and 10, the dividing lines are positioned perpendicular to the direction of leaf motion. This allows leaves to be positioned along the edge to minimize under dosage at the dividing line due to match line (i.e., junction) effects. If the dividing line is instead parallel to the leaf motion direction and positioned along a leaf side, under dosage may result. The under dosage may not be corrected for since the leaves can not move perpendicular to the dividing line. The leaves used to define the dividing line are preferably offset slightly from the line to leave a margin adjacent to the line. This is used to correct for under dosages that can occur at the dividing line.

Figure 11:
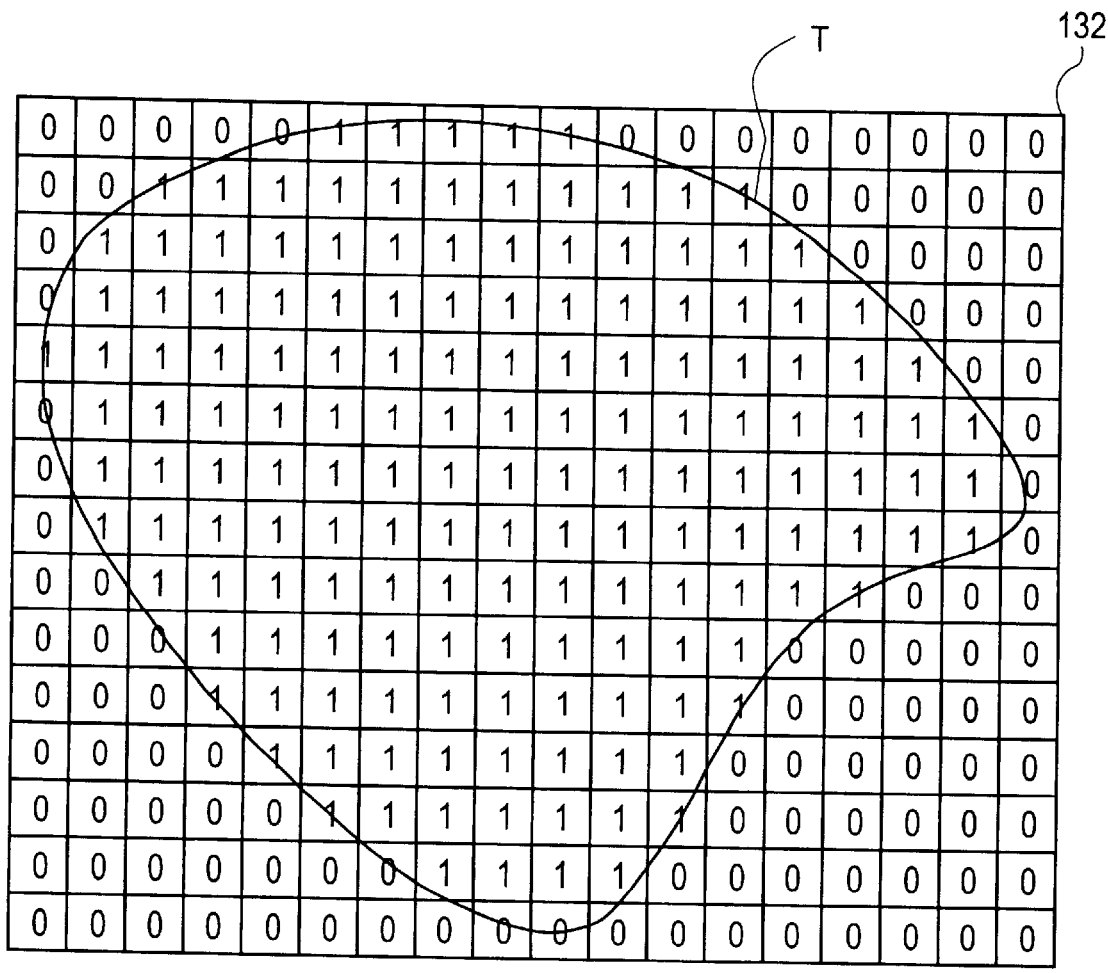
FIG. 11 is a plan view of a treatment area with a grid placed over the treatment area to define cells within the treatment area.

While the above described method works well for treatment areas having borders with relatively small slopes and smooth transitions between direction changes, a preferred method for treatment areas having irregular borders is to place a grid over the treatment area and define a plurality of intensity cells within the treatment area to determine the appropriate leaf positions. As shown in FIG. 11, a grid 132 is placed over the treatment area T with the squares positioned to line up with the leaves in each of the two orthogonal collimator orientations. The cells of the grid 132 preferably have one side with a length equal to a fraction (1/n, where n is an integer) of the width of the collimator leaves. The other side of the cell may have a smaller or larger value of n in the 1/n fraction of the leaf width, as described below. For example, the treatment area may be subdivided into 5 mm×5 mm cells or 2 mm×5 mm cells for use with a multi-leaf collimator having 1 cm leaf widths. Other grid sizes may be used with leaves having different widths.

All cells located within the treatment area T receive half of the prescribed dosage in each collimator orientation. These cells are identified with a "1" in FIG. 11. The cells located completely outside of the treatment area T do not receive any radiation. These cells are identified with a "0" in FIG. 11. Those cells located on the border of the treatment area T receive either full radiation or zero radiation, depending on how much of the cell is located within the treatment area. If fifty percent or more of the cell is located within the treatment area T, the cell will receive full radiation, if less than fifty percent of the cell is located within the treatment area, the entire cell will receive no radiation.

Figure 12:
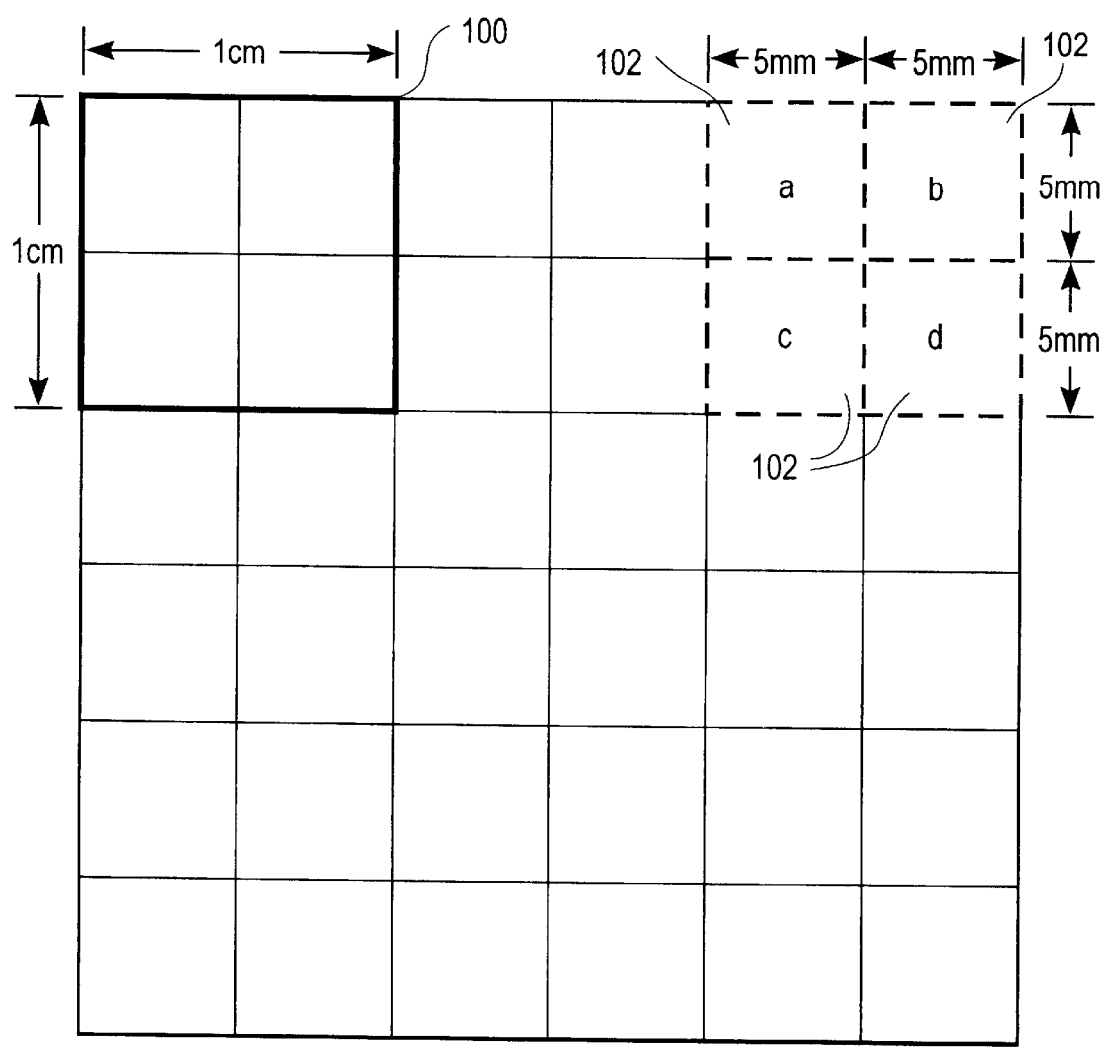
FIG. 12 is a schematic illustrating the cells of FIG. 11 located in an intensity map.

FIG. 12 shows an intensity map having a plurality of 1 cm×1 cm macrocells 100 (indicated by dark lines) divided into four 5 mm×5 mm microcells 102 (indicated by dashed lines). The 5 mm×5 mm microcells 102 are used to convert macrocell 100 into two orthogonal intensity maps, one with a resolution of 5 mm×10 mm, and the other with a resolution of 10 mm×5 mm. An example of a process for dividing the intensity map into groups of four 5 mm×5 mm microcells 102 is described in U.S. patent application Ser. No. 09/234,364, now U.S. Pat. No. 6,134,296, by Siochi, filed Jan. 20, 1999, which is incorporated herein by reference in its entirety. This grouping of 5 mm×5 mm microcells 102 allows for treatment of a field with a 5 mm×5 mm resolution using a multi-leaf collimator having one centimeter leaves, as shown in FIG. 3.

Figure 13:
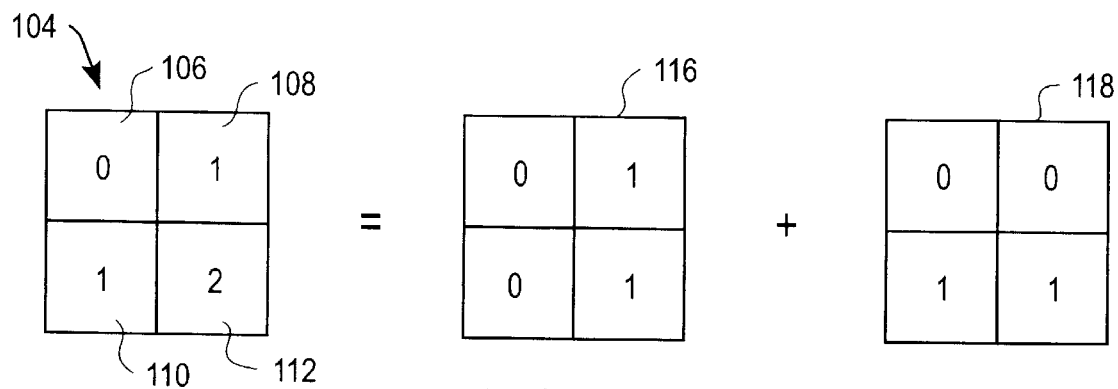
FIG. 13 is a diagram of a matrix broken down into a zero degree matrix component and a ninety degree matrix component.
Figure 14:
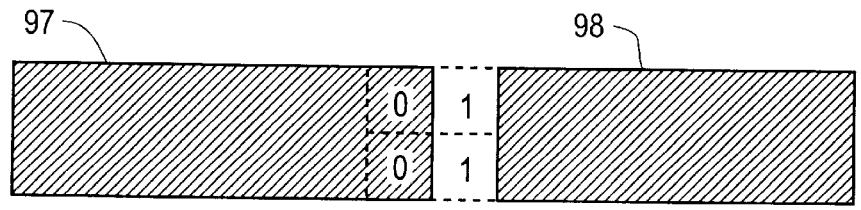
FIG. 14 is a plan view of an opposing pair of leaves configured to apply a dosage specified by the zero degree matrix of FIG. 13.
Figure 15:
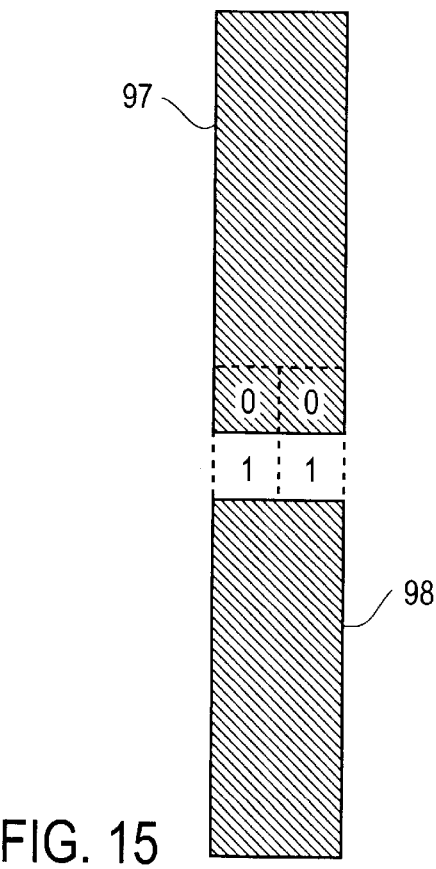
FIG. 15 is a plan view of an opposing pair of leaves configured to apply a dosage specified by the ninety degree matrix of FIG. 13.

FIG. 13 illustrates an example of a matrix, generally indicated at 104 formed from an intensity map composed of four 5 mm×5 mm microcells 106, 108, 110, 112. Each microcell 106, 108, 110, 112 identifies a section in a field to be treated with radiation. The numbers (0, 1, 1, 2) within each microcell 106, 108, 110, 112, respectively, represent the radiation intensity level for locations within the field and are in monitor units (mu) or relative monitor unit intensities (e.g., 1×10$^2$ mu). In order to provide 5 mm×5 mm resolution for the intensity map, the matrix 104 is broken down into two orthogonal matrices, 116, 118 having a 1 cm×5 mm resolution and 5 mm×1 cm resolution, respectively. A one centimeter leaf width multi-leaf collimator may then be used to deliver the intensity map with a 5 mm×5 mm resolution. For example, a pair of leaves 97, 98 positioned as shown in FIG. 14 may be used to deliver the intensity map shown in matrix 116 of FIG. 13. A dose of radiation (e.g., 1 mu) is applied to fields corresponding to microcells 108 and 112 of matrix 104. The collimator is then rotated approximately ninety degrees to deliver the intensity map shown in matrix I 18 with the leaf position shown in FIG. 15. With the collimator rotated ninety degrees, a dose of radiation (e.g., 1 mu) is applied to the fields corresponding to microcells 110 and 112 of matrix 104. The two radiation applications result in a 2 mu dose to the field corresponding to microcell 112, a 1 mu dose to the fields corresponding to microcells 108 and 110, and no radiation being applied to the field corresponding to microcell 106. The decomposition of the matrix 104 into orthogonal matrices 116 and 118 thus provides for 5 mm×5 mm resolution treatment using collimator leaves having a one centimeter width.

The intensity map is decomposed to define two orthogonal maps, a zero degree map for application with a zero degree offset collimator setting, and a ninety degree map for application with an orthogonal collimator setting. In the following description, the original input intensity map is defined as a macromatrix and the groups of four microcells within the macromatrix are defined as micromatrices (or matrices). In order for the intensity map to be decomposed into orthogonal maps, the vertical gradients of each column of the micromatrix (matrix) 100 must be equal to one another and the horizontal gradients of each row of the micromatrix must also be equal to one another (FIG. 12). This provides a 1 cm×1 cm area under the intersection of one leaf pair for one collimator setting and another leaf pair for the orthogonal collimator setting. For example, if the horizontal gradients are equal for the micromatrix having cells 102 (shown in FIG. 12) the following equation must apply:

$$b-a=d-c;$$

where: a, b, c, d are the intensity values
corresponding to locations in the micromatrix 102 of FIG. 12

Similarly, if the vertical gradients are equal the following equation must apply:

$$c-a=d-b.$$

A method for converting an intensity map which does not meet the above constraints (i.e., horizontal gradients for each row are not equal or vertical gradients for each column are not equal), into an intensity map having equal horizontal and vertical gradients is described in U.S. patent application Ser. No. 09/457,601, filed Dec. 8, 1999, which is incorporated by reference herein in its entirety. Several decompositions of an intensity map are possible to create the two orthogonal maps. An optimization method such as described in U.S. patent application Ser. No. 09/457,602, now U.S. Pat. No. 6,314,159, filed Dec. 8, 1999 (incorporated by reference herein in its entirety) may be used to find a decomposition which yields the shortest treatment delivery time to minimize overall treatment time and increase the life of the radiation treatment device, for example.

The intensity map may be broken down into microcells having a dimension other than 5 mm×5 mm if a different resolution is required. For example, each macrocell may be divided into nine microcells in which case the intensity map may be deliverable as two orthogonal intensity maps having a resolution of 1 cm×⅓ cm and ⅓ cm×1 cm (see, for example, U.S. patent application Ser. No. 09/234,364, now U.S. Pat. No. 6,134,296, referenced above). Also, a multi-leaf collimator having leaves with a width other than 1 cm may be used, and the size of the corresponding microcells will be 1/n times the leaf width (where n is a positive integer (e.g., 2 or 3).

Figure 16:
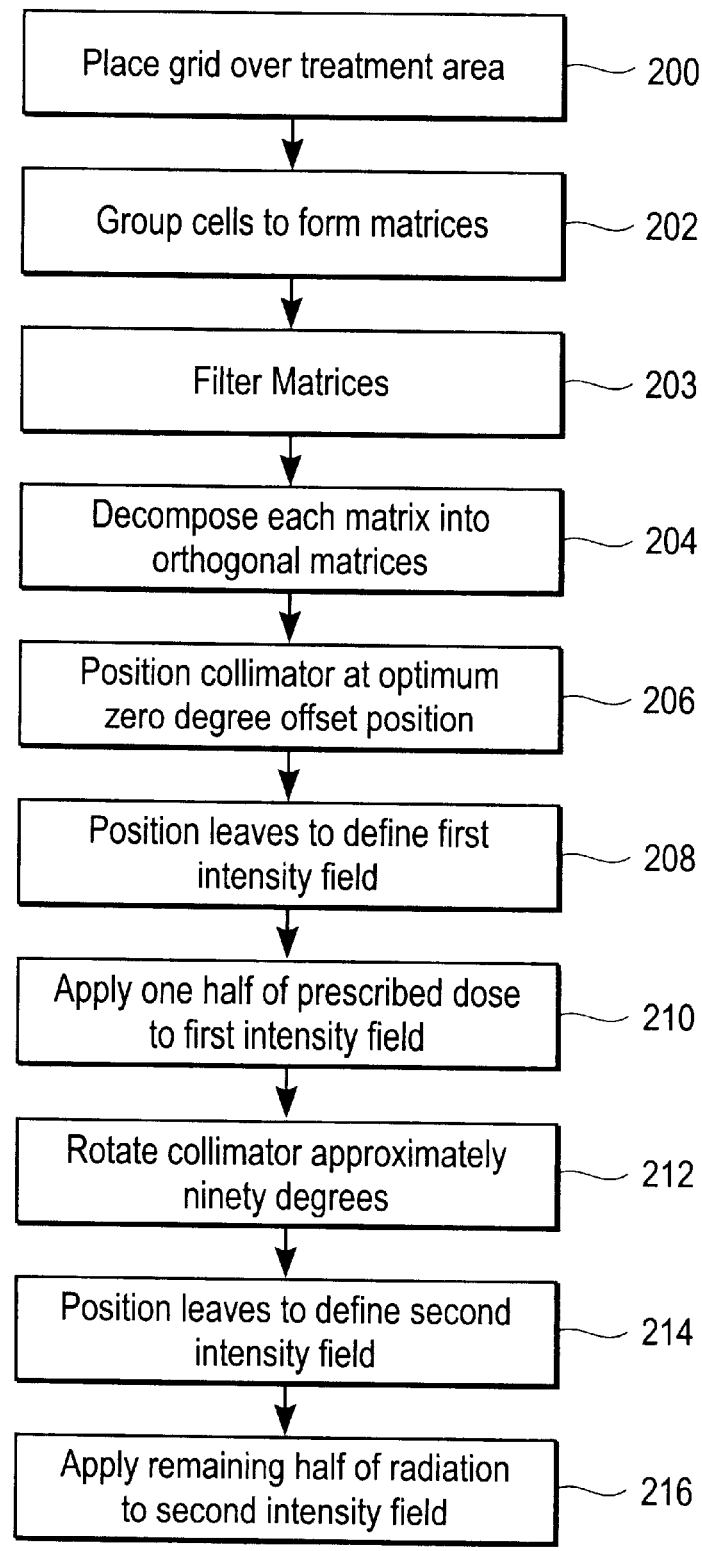
FIG. 16 is a flowchart illustrating a process for defining an intensity map for a treatment area and delivering radiation to the treatment area.

FIG. 16 is a flow chart illustrating a process for defining and delivering radiation treatment fields with an intensity modulating multi-leaf collimator. At step 200, a grid 132 is placed over the treatment area T (FIGS. 11 and 16). As described above, the grid 132 preferably includes cells having sides equal to an integral fraction (i.e., 1/n, where n is an integer) of the width of the multi-collimator leaves. At step 202 the cells are grouped to form matrices. At step 203, the matrices are filtered as described in U.S. patent application Ser. No. 09/457,601 to be compatible with the decomposition process. Each matrix is decomposed into orthogonal matrices (step 204). The collimator is then rotated about central axis R to its optimum zero degree offset position (step 206). With the collimator in its zero degree offset orientation, leaves are moved longitudinally to define a first treatment field (step 208). One half of the prescribed dose of radiation is applied to the first treatment field (step 210). The collimator is then rotated approximately ninety degrees about central axis R (step 212) and the leaves are positioned to define a second treatment field (step 214). The remaining half of the radiation is then applied with the leaves positioned for the second treatment field (step 216). The leaves may also be positioned to define additional treatment fields if required by the decomposition of matrices as shown in FIG. 13.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for delivering radiation from a radiation source to a treatment area utilizing a multi-leaf collimator, comprising:

positioning the multi-leaf collimator between the radiation source and the treatment area to block a portion of the radiation, with leaves of the multi-leaf collimator extending longitudinally along a first axis and being positioned to define a first treatment field;

delivering radiation to said first treatment field;

rotating the multi-leaf collimator about a central axis extending generally perpendicular to a plane containing at least a portion of the leaves;

positioning the leaves to define a second treatment field; and delivering radiation to said second treatment field;

wherein positioning the leaves comprises intersecting a periphery edge of the target area at a transverse edge of each of the leaves at a predetermined location based on the number of treatment fields.

2. The method of claim 1 wherein rotating the multi-leaf collimator comprises rotating the collimator until the leaves extend longitudinally along a second axis generally perpendicular to said first axis.

3. The method of claim 1 wherein delivering radiation to said first treatment field comprises delivering one half of a prescribed radiation dose and delivering radiation to said second treatment field comprises delivering a remaining half of the prescribed radiation dose.

4. The method of claim 1 further comprising longitudinally moving the leaves to define a third treatment field and delivering radiation to said third treatment field.

5. The method of claim 4 wherein delivering radiation to said first, second, and third treatment fields comprises delivering one-third of a prescribed radiation dose to each treatment field.

6. A method for delivering radiation from a radiation source to a treatment area utilizing a multi-leaf collimator, comprising:

positioning the multi-leaf collimator between the radiation source and the treatment area to block a portion of the radiation, with leaves of the multi-leaf collimator extending longitudinally along a first axis and being positioned to define a first treatment field;

delivering radiation to said first treatment field;

rotating the multi-leaf collimator about a central axis extending generally perpendicular to a plane containing at least a portion of the leaves;

positioning the leaves to define a second treatment field; and delivering radiation to said second treatment field;

wherein positioning the leaves to define said second treatment field comprises intersecting a periphery edge of the target area at a transverse edge of each of the leaves at a position spaced one-third times the width of the leaf from a longitudinal edge of the leaf.

7. The method of claim 6 wherein moving the leaves to define said third treatment field comprises intersecting the periphery edge of the target area at the transverse edge of the leaf at a position spaced two-thirds times the width of the leaf from the longitudinal edge of the leaf.

8. The method of claim 6 further comprising repeating positioning the multi-leaf collimator, positioning the leaves, and delivering radiation for four treatment fields.

9. A method for delivering radiation from a radiation source to a treatment area utilizing a multi-leaf collimator, comprising:

dividing said treatment area into a plurality of cells each having a defined treatment intensity level;

grouping the cells to form a plurality of matrices, each of the matrices having at least one dimension approximately equal to a width of the collimator leaf;

decomposing each of the matrices into orthogonal matrices to identify a plurality of treatment fields;

positioning the multi-leaf collimator between the radiation source and the treatment area to block a portion of the radiation, with leaves of the multi-leaf collimator extending longitudinally along a first axis and being positioned to define a first treatment field;

delivering radiation to said first treatment field;

rotating the multi-leaf collimator about a central axis extending generally perpendicular to a plane containing at least a portion of the leaves;

positioning the leaves to define a second treatment field; and delivering radiation to said second treatment field.

10. The method of claim 9 wherein radiation is delivered with a resolution one half times the leaf width.

11. The method of claim 9 further comprising assigning an intensity level greater than zero to each cell located entirely within the treatment area and assigning an intensity level of zero for each cell located completely outside of the treatment area.

12. The method of claim 11 further comprising assigning an intensity level greater than zero to each cell having one half or greater of its area located within the treatment area and assigning an intensity level of zero to each cell having less than one half of its area located within the treatment area.

13. The method of claim 9 wherein the collimator leaves have a width of 1 cm and the cells are approximately 1 cm×5 mm.

14. The method of claim 9 wherein positioning the leaves comprises intersecting a periphery edge of the treatment area with a midpoint of a transverse edge of each leaf.

15. A method for delivering radiation from a radiation source to a treatment area utilizing a multi-leaf collimator, comprising:

dividing the treatment area into two or more sections, the area being divided along a line extending generally perpendicular to a direction of travel of the leaves;

positioning the multi-leaf collimator between the radiation source and the treatment area to block a portion of the radiation, with leaves of the multi-leaf collimator extending longitudinally along a first axis and being positioned to define a first treatment field;

delivering radiation to said first treatment field;

rotating the multi-leaf collimator about a central axis extending generally perpendicular to a plane containing at least a portion of the leaves;

positioning the leaves to define a second treatment field; and delivering radiation to said second treatment field.

16. The method of claim 15 wherein positioning the leaves comprises intersecting a periphery edge of the treatment area with a midpoint of a transverse edge of each leaf.

17. The method of claim 15 wherein delivering radiation to said first treatment field comprises delivering one half of a prescribed radiation dose and delivering radiation to said second treatment field comprises delivering a remaining half of the prescribed radiation dose.

18. The method of claim 15 further comprising longitudinally moving the leaves to define a third treatment field and delivering radiation to said third treatment field.

\* \* \* \* \*